United States Patent
Chinkov et al.

(10) Patent No.: US 8,283,502 B2
(45) Date of Patent: *Oct. 9, 2012

(54) AUTOCATALYTIC PROCESS FOR THE SYNTHESIS OF CHIRAL PROPARGYLIC ALCOHOLS

(75) Inventors: Nicka Chinkov, Mishmar Haemek (IL); Aleksander Warm, Arbaz (CH); Erick Carreira, Zürich (CH)

(73) Assignee: Lonza Ltd., Visp (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/740,617

(22) PCT Filed: Apr. 9, 2010

(86) PCT No.: PCT/EP2010/002224
§ 371 (c)(1),
(2), (4) Date: Apr. 29, 2010

(87) PCT Pub. No.: WO2010/115638
PCT Pub. Date: Oct. 14, 2010

(65) Prior Publication Data
US 2012/0029237 A1    Feb. 2, 2012

Related U.S. Application Data

(60) Provisional application No. 61/167,920, filed on Apr. 9, 2009.

(30) Foreign Application Priority Data

Apr. 9, 2009   (EP) .................................. 09005213

(51) Int. Cl.
C07C 33/00   (2006.01)
C07C 215/00   (2006.01)
(52) U.S. Cl. ........................ 568/807; 564/442; 564/443
(58) Field of Classification Search .................. 564/442, 564/443; 568/807
See application file for complete search history.

(56) References Cited

FOREIGN PATENT DOCUMENTS

| WO | 9520389 | 8/1995 |
|---|---|---|
| WO | 9637457 | 11/1996 |
| WO | 9830540 | 7/1998 |
| WO | 9830543 | 7/1998 |
| WO | 9851676 | 11/1998 |
| WO | 2004087628 | 10/2004 |

OTHER PUBLICATIONS

Jiang et al., "Zn(II)-Mediated Alkynylation-Cyclization of o-Trifluoroacetyl Anilines: One-Pot Synthesis of 4-Trifluoromethyl-Substituted Quinoline Derivatives", J. Org. Chem, vol. 67, pp. 9449-9451; 2002.

Jiang et al., "Alkynylation of Carbonyl Compounds with Terminal Acetylenes Promoted by ZnCl2 and Et3N: Simple, Mild and Efficient Preparation of Propargylic Alcohols", Tetrahedron Letters, vol. 43, pp. 8323-8325; 2002.

*Primary Examiner* — Porfirio Nazario Gonzalez
(74) *Attorney, Agent, or Firm* — Hoffmann & Baron, LLP

(57) ABSTRACT

An autocatalytic process for the synthesis of chiral propargylic alcohols.

12 Claims, No Drawings

AUTOCATALYTIC PROCESS FOR THE SYNTHESIS OF CHIRAL PROPARGYLIC ALCOHOLS

This application is the U.S. National Phase of, and Applicants claim priority from, International Application Number PCT/EP2010/002224 filed 9 Apr. 2010, and U.S. Provisional Patent Application bearing Ser. No. 61/167,920 filed 9 Apr. 2009 and European Patent Application No. 09005213.5 filed 9 April, 2009, which are incorporated herein by reference in their entirety.

The invention is directed to an autocatalytic process for the preparation of chiral propargylic alcohols, which are key intermediates for the preparation of pharmaceuticals and agrochemicals and as precursors for compounds in the materials sciences.

Jiang et al. disclosed in *Tetrahedron Lett.* 2002, 43, 8323-8325 and *J. Org. Chem.* 2002, 67, 9449-9451 the reaction of acetylene derivatives with aldehydes and ketones in the presence of equimolar amounts of a zinc(II) compound (Zn(II) compound) to give several racemic propargylic alcohols. Chiral compounds are not mentioned at all.

WO-A-95/20389, WO-A-96/37457, WO 98/30543 and WO 98/30540 disclose several processes for the production of chiral propargylic alcohols useful for the synthesis of pharmaceuticals. WO-A-98/51676 disclose a process wherein by addition of a first chiral and optionally a second additive in a zinc(II) mediated reaction the chiral product is obtained in high enantiomeric excess. The disadvantage of said process is the use of high amounts of expensive zinc catalysts and chiral compounds.

WO-A-2004/87628 further discloses facultative use of a chiral auxiliary in an equivalent molar amount in respect of the zinc(II) compound for the production of chiral propargylic alcohols mentioned above.

A main task for the present invention was therefore to supply an alternative process for the production of chiral propargylic alcohol with high enantiomeric excess. A further problem was to reduce the amounts of catalyst and other components to be added during the reaction in order to facilitate the workup procedures of the product and to promote industrial production.

DESCRIPTION OF THE INVENTION

The problem is solved by the process of claim 1. The inventive process comprises the addition of an initial amount of the chiral product to the reaction as a chiral mediator, which allows to reduce the amount of further chiral auxiliaries. Presence of the chiral product from the beginning of the reaction has the advantageous side effect that the amount of the zinc(II) catalyst can be reduced compared to processes known in the art. Furthermore, the addition of the compound of formula I allows to dispense with chiral auxiliaries, while still the chiral product is formed in high enantiomeric excess (ee).

Claimed is a process for the preparation of chiral compounds of the formula

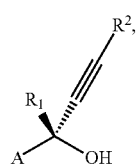

I or mirror image
wherein $R^1$ is selected from the group consisting of hydrogen, $C_{1-6}$-alkyl or $(C_{1-6}$-alkoxy)carbonyl, any of said alkyl or alkoxy optionally is substituted with one or more halogen atoms, and $R^2$ is selected from the group consisting of aryl, aralkyl, $C_{1-6}$-alkyl and $(1'$-$R^3)$—$C_{3-6}$-cyclo-alkyl wherein $R^3$ is hydrogen, methyl or ethyl, any of said aryl, aralkyl or alkyl is optionally substituted with one or more halogen atoms, and A is selected from the group consisting of $C_{1-20}$-alkyl, $C_{3-6}$-cycloalkyl, aryl and aralkyl, any of said cycloalkyl, aryl or aralkyl is optionally annellated to one or more further 5 to 7 membered carbocyclic or heterocyclic rings, and/or any of said alkyl, cycloalkyl, aryl or aralkyl is optionally substituted with one or more halogen atoms, cyano, $C_{1-6}$-alkyl, $C_{3-6}$-cycloalkyl, —$NR^4R^5$, —$SR^6$ and/or —$OR^7$, and wherein said $C_{1-6}$-alkyl or $C_{3-6}$-cycloalkyl substituent optionally attached to A is further optionally substituted with one or more halogen atoms, and wherein $R^4$ and $R^5$ independently are hydrogen or $C_{1-6}$-alkyl, or wherein $R^4$ is hydrogen and $R^5$ is $C_{2-7}$-acyl or $(C_{1-6}$-alkoxy) carbonyl, wherein any of said acyl and/or alkoxy in $R^5$ optionally is substituted with one or more halogen atoms, or wherein $R^4$ and $R^5$ together with the nitrogen atom form a 5 to 7 membered heterocyclic ring, or wherein $R^4$ and $R^5$ together are =CH-aryl, the aryl moiety optionally being substituted with one or more halogen atoms, —$NH_2$, —$NH(C_{1-6}$-alkyl), —$N(C_{1-6}$-alkyl)$_2$ or $C_{1-6}$-alkyl, or $R^4$ and $R^5$ together are =CH—$N(C_{1-6}$-alkyl)$_2$, and wherein $R^6$ is $C_{1-6}$-alkyl, optionally substituted with one or more halogen atoms, and wherein $R^7$ is hydrogen or $C_{1-6}$-alkyl, optionally substituted with one or more halogen atoms, or wherein A and $R^1$ together form a 5 to 7 membered carbocyclic or heterocyclic rings, optionally substituted with one or more halogen atoms, cyano, $C_{1-6}$-alkyl, $C_{3-6}$-cycloalkyl, —$NR^4R^5$, —$SR^6$ and/or —$OR^7$, wherein $R^3$, $R^4$, $R^5$, $R^6$ and $R^7$ are as defined above, said process comprising the steps of (i) preparing a mixture of a zinc(II) catalyst, an initial amount of the compound of formula I in a molar ratio to the zinc(II) catalyst from 0.1:1 to 2:1, and optionally a further chiral auxiliary in a molar ratio to the zinc(II) catalyst from 0.1:1 to 3:1, and (ii) adding to said mixture (a) a compound of formula

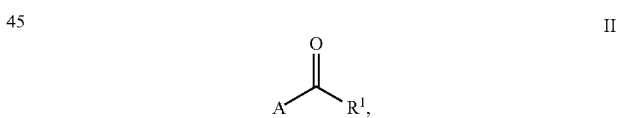

II wherein A and $R^1$ are as defined above, (b) a base, and (c) a compound of formula

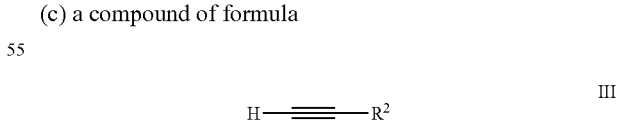

III wherein $R^2$ is as defined above, at a mixing temperature from −78 to 10° C., and (iii) heating the mixture obtained in step (ii) to 10 to 50° C. until completion of the reaction, to obtain the compound of formula I.

Here and hereinbelow the term "alkyl" represents a linear or branched alkyl group. By using the form "$C_{1\text{-}n}$-alkyl" the alkyl group is meant having 1 to n carbon atoms. $C_{1-8}$-alkyl represents for example methyl, ethyl, propyl, isopropyl, butyl, isobutyl, sec-butyl, tert-butyl, as well as linear and branched pentyl, hexyl, heptyl and octyl.

Here and hereinbelow the term "alkoxy" represents a linear or branched alkoxy group. By using the form "$C_{1-n}$-alkoxy" the alkyl group is meant having 1 to n carbon atoms.

$C_{1-6}$-alkoxy represents for example methoxy, ethoxy, propoxy, isopropoxy, butoxy, isobutoxy, sec-butoxy, tert-butoxy, as well as linear and branched pentyloxy and hexyloxy.

Here and hereinbelow the term "cycloalkyl" represents a cycloaliphatic group having 3 carbon atoms or more. Cycloalkyl represents mono- and polycyclic ring systems such as cyclopentyl, cyclohexyl, cycloheptyl, cyclooctyl, adamantyl or norbornyl.

Here and hereinbelow the term "aryl" represents an aromatic group, preferably phenyl or naphthyl.

Here and hereinbelow the term "aralkyl" represents a group having 7 or more carbon atoms, consisting of an alkyl and an aryl moiety, wherein the alkyl moiety of the aralkyl residue is a $C_{1-8}$ alkyl group and the aryl moiety is selected from the group consisting of phenyl, naphthyl, furanyl, thienyl, benzo[b]furanyl, benzo[b]thienyl.

Regarding the addition of compounds in step (ii) the inventive process does not rely on a specific order of addition. In a preferred embodiment the compounds of formula II and the base are added simultaneously, either separately or as a mixture. The compound of formula II may also be added before or after the addition of compound formula III or both compounds may be added simultaneously, either separately or as a mixture. In the latter case preferably the compound of formula II is fed together with the base.

The process is designed to obtain the compound of formula I with an enantiomeric excess (ee) of at least 40%, preferably with an ee of at least 60%, more preferred of at least 80%, and even more preferred of at least 90%.

In a preferred embodiment the reaction is carried out in the presence of a proton source selected from the group consisting of $C_{1-6}$-alcohols, phenols, benzyl alcohols, and linear or branched $C_{2-5}$-alkanoic acids, each of said $C_{1-6}$-alcohols, phenols and benzyl alcohols optionally being substituted with one or more halogen atoms, nitro, methyl or aryl groups, said $C_{2-5}$-alkanoic acid optionally being substituted with one or more halogen atoms. Both the alcohol and the acid facilitate the proton exchange. Especially the addition of the acid is not intended to change the pH of the solution. The alcohol and the acid may be added at any time before completion of the reaction.

Preferably the zinc(II) catalyst is used in the process in a total molar ratio to the compound of formula II from 0.1:1 to 0.3:1. By using the product itself as the main chiral auxiliary the amount of the zinc(II) catalyst needed in the reaction can be reduced remarkably compared to processes known in the art. The compound of formula I mediates the catalytic process and although the zinc(II) catalyst and the compound of formula I form a zinc(II) complex with a certain stoichiometry it is not necessary to add the chiral compound of formula I and the zinc(II) catalyst in equimolar amounts. Preferably the amount of the initially added compound of formula I is higher than the amount of the zinc(II) catalyst.

Suitable zinc(II) catalysts are for example di($C_{1-4}$-alkyl)zinc, diphenylzinc, $Zn(OTf)_2$ and $ZnCl_2$, wherein the alkyl moieties are independently selected from the group consisting of methyl, ethyl, propyl, isopropyl, butyl, isobutyl, sec-butyl and tert-butyl. OTf denotes a triflate (trifluoromethanesulfonate) group.

In a preferred embodiment the compound of formula I used as an auxiliary in step (i) is added in a molar ratio to the compound of formula III from 0.1:1 to 0.45:1. The compound of formula I and the zinc(II) catalyst are part of an chiral zinc(II) complex mediating an autocatalytic process. Autocatalysis in the present Zn(II) mediated autocatalytic process has the meaning that a chiral zinc(II) complex promotes the reaction in such a way, that the reaction may carried out in the absence of any further chiral auxiliary. Chiral compounds of formula I for use as initial amount may be obtained by production of racemic compounds and subsequent chiral resolution. Although said zinc(II) complex has a certain stoichiometry it is not necessary to add the chiral compound of formula I, or any optionally further auxiliary, and the zinc(II) catalyst in equimolar amounts.

In a preferred embodiment the compound of formula I used as an auxiliary in step (i) is added in a molar ratio to the compound of formula III from 0.1:1 to 0.45:1.

A chiral auxiliary may be used to increase the meditative effect of the compound of formula I to give the desired enantiomer of formula I. Preferably the auxiliary is selected from the group consisting of [R—(R,S)]-β-methyl-α-phenyl-1-pyrrolidineethanol ((1R,2S)-pyrrolidinylnorephedrine=(1R,2S)-PNE), N-methylephedrine, ephedrine, N,N-dibenzoylephedrine, norephedrine, diethyl tartate, (1R,2R)-pseudoephedrine, cinchonine, (1S,2S)—N-methylpseudoephedrine, 2-(pyrrolidin-1-yl)ethanol, and N,N-dibutyl-2-amino-ethnol. (1R,2S)-PNE is a preferred auxiliary.

In a preferred embodiment in step (ii) the compound of formula II is used in a molar ratio to the compound of formula III from 0.8:1 to 3:1.

Addition of the compound of formula III can be carried out at a temperature from −78 to +30° C.

In a preferred embodiment the compounds of formula II are selected from the group consisting of p-methylbenzaldehyde, p-fluorobenzaldehyde, p-cyanobenzaldehyde, p-methoxybenzaldehyde, naphthalenealdehyde, cinnamaldehyde, $C_{3-20}$-alkane aldehydes, cycloheane carbaldehyde, cyclohexyl methyl ketone, methyl 4-methylcyclohexyl ketone, 1,1,1-trifluoroacetophenone and 2-(trifluoroaceto)-4-chloroanilin.

In a further preferred embodiment the base is added in a molar ratio to the compound of formula III from 0.5:1 to 3:1.

Addition of the base can be carried out at a temperature from −40 to +10° C. In a preferred embodiment the compounds of formula III are selected from the group consisting of $C_{1-6}$-alkane acetylenes, cyclopropylacetylene, (1'-methyl)-cyclopropyl-acetylene and phenylacetylene.

A suitable base for the present process is a strong base such as sodium hydroxide, potassium hydroxide, caesium hydroxide, sodium hydride, potassium hydride, trimethylamine, triethylamine, potassium trimethylsilanolate, lithium trimethylsilanolate, lithium tert-butoxylate, lithium 2,2,2-trifluoroethoxylate, butyllithium and hexyllithium.

Preferably the base is an organometallic compound or a lithium organic salt.

In a preferred embodiment such organometallic lithium compound is selected from the group consisting of phenyllithium and ($C_{1-8}$-alkyl)lithium, such as methyllithium, ethyllithium, n-propyllithium, n-butyllithium (BuLi), n-hexyllithium (HexLi) or n-octyllithium.

In a further preferred embodiment the lithium organic salt is a lithium $C_{1-6}$-alkoxide.

Expediently, an organometallic lithium compound or lithium organic salt is used in the presence of a Lewis base or a nitrogen ligand such as diethyl ether, tetrahydrofuran (THF), tetramethylenediamine (TMEDA), N,N,N',N',N''-pentamethyldiethylenetriamine (PMDTA), or a sparteine such as (−)-sparteine, to deaggregate the lithium compound.

During the addition of the base the reaction mixture is preferably kept at a temperature from −40 to +10° C.

The inventive process may be carried out with or without solvent. In a preferred embodiment the process is carried out in an aprotic polar, a non-polar solvent or a mixture of aprotic polar and/or non-polar solvents.

The solvents of agents added in solution may be selected independently of each other. Particularly preferred the solvent is selected from the group consisting of tetrahydrofuran (THF), benzene, chlorobenzene, o-, m-, p-dichlorobenzene, dichloromethane, toluene, hexanes, cyclohexane, pentane, 1,4-dioxane, cyclohexane, diethyl ether, tert-butyl methyl ether, diisopropyl ether, N-methylpyrrolidine or a mixture thereof.

If a $C_{1-6}$-alcohol is added as a proton source said $C_{1-6}$-alcohol is selected from the group consisting of methanol, ethanol, propanol, isopropyl alcohol, butanol, isobanol, sec-butanol, tert-butanol, pentanol, $(CH_3)_3CCH_2OH$, $(CH_3)_3CCH(CH_3)OH$, $Cl_3CCH_2OH$, $CF_3CH_2OH$, $CH_2=CHCH_2OH$, $(CH_3)_2NCH_2CH_2OH$. Examples for suitable benzyl alcohols and phenols are phenol, $PhCH_2OH$, $Ph_3COH$, 4-Cl-phenol and 4-$NO_2$-phenol.

In a further preferred embodiment a $C_{2-5}$-alkanoic acid added as a proton source is selected from the group consisting of acetic acid, prioponic acid, butyric acid, $CF_3CO_2H$, $CH_3CHClCOOH$ and $(CH_3)_3CCO_2H$.

EXAMPLES

For calculation of the yield of the product, as well as for the calculation of the enantiomeric excess the product added in step (i) of the process is subtracted.

Comparison Example 1

Racemic 2,4-diphenyl-but-3-yn-2-ol

THF and toluene were purified by distillation and dried by passage over activated alumina under an argon atmosphere ($H_2O$ content <30 ppm, Karl Fischer titration). Solvents were degassed prior to use. Phenylacetylene was purified by transfer via neutral alumina prior to use. (1S,2R)-1-Phenyl-2-(pyrrolidin-1-yl)propan-1-ol ((1S,2R)-PNE, was prepared according to *Organic Synthesis*, 2000, 77, 12-21. Acetophenone was stirred over $CaSO_4$ several hours prior to use. 2,4-Diphenyl-but-3-yn-2-ol (S-(1)) and its enantiomer R-(1) were obtained by preparative chiral resolution of the racemate.

Example 1

2,4-diphenyl-but-3-yn-2-ol (S-(1))

A solution of $Et_2Zn$ (0.24 eq, 0.48 mmol, 1.1 M in toluene) is dropwise added to a mixture of (1R,2S)—N-pyrrolidinyl-norephedrine (1S,2R)-PNE, 123.2 mg, 0.3 eq, 0.6 mmol, in 0.5 mL THF) and chirally pure 2,4-diphenyl-but-3-yn-2-ol (S-(1)) (0.18 eq, 0.36 mmol, 80.02 mg) at 17° C. After 30 min of stirring at r.t. phenylacetylene (III) (1.5 eq, 3 mmol, 0.33 mL in 0.1 mL toluene) is added dropwise at 15° C. and the mixture is stirred for additional 1.5 h at r.t. Acetophenone (a compound of formula II) (1 eq, 2 mmol, 0.23 mL in 0.4 mL THF)) is added at 5° C. within 30 min by means of syringe pump, followed by 12 h addition of hexyllithuim (HexLi)(1 eq, 2.3 M in toluene, 0.87 mL) at −5° C. to 10° C. At the completion of base addition the reaction mixture is stirred 1 h at r.t., and then heated to 40° C. After 9 h of stirring at 40° C. the reaction is quenched with citric acid (pH=4 to 6), the aqueous phase is extracted with EtOAc (3 times), washed with brine, dried over $MgSO_4$, concentrated and chromatographed on silica gel (hexane/EtOAc=15:1) to give the corresponding tertiary alcohol S-(1) or R-(1) for qualitative identification by NMR. Until completion of the reaction at certain reaction times, 0.5 mL aliquots are collected, each quenched by citric acid (pH=4 to 5), diluted by EtOAc, the organic phase is dried over $MgSO_4$, transferred via silica gel, concentrated and diluted by Hex/iPrOH=95:5 (w/w). The enantiomeric excess of the residue is determined by HPLC analysis (Chiracel OD-H, 0.46 cm×25 cm; hexane:iPrOH=95:5 (w/w), flow=1 mL/min, retention time of the enantiomers: t=13.95 and 19.25 min). After 3 h 2,4-diphenyl-but-3-yn-2-ol (S-(1)) is obtained with 68% conversion (Con.), 76.6% selectivity (Sel.) and 62% enantiomeric excess (ee).

$^1H$ NMR (300 MHz, $CDCl_3$) d 7.76 (d, J=6.9 Hz, 2H), δ 7.5-7.3 (m, 8H) d 2.5 (s, 1H), d 1.88 (s, 3H);

$^{13}C$ NMR (75 MHz, $CDCl_3$) δ 145.5, 131.6, 128.4, 128.2, 128.1, 127.6, 124.9, 122.4, 92.3, 84.9, 70.4, 33.4.

Example 2

2,4-diphenyl-but-3-yn-2-ol (R-(1))

Example 1 is repeated except by adding 2,4-diphenyl-but-3-yn-2-ol (R-(1)) as the chiral compound of formula I. After 3 h 2,4-diphenyl-but-3-yn-2-ol (R-(1)) is obtained with 68.5% Con., 76.5% Sel. and 57.3% (ee), accordingly.

Example 3

$Et_2Zn$ (DEZ, 0.24 eq), 2,4-diphenyl-but-3-yn-2-ol (R-(1)) as chiral mediator (0.48 eq), phenylecetylene (a compound of formula III) (2.0 eq), acetophenone (a compound of formula II) (1.0 eq) and HexLi (1 eq) are reacted as described in example 1 wherein the base is added within 16 h and subsequently heating the mixture to 40° C. Toluene is added to prevent aldolization. The reaction yields 2,4-diphenyl-but-3-yn-2-ol (R-(1)): 3 h aliquot, 72.2% Con., 77.1% Sel. 44.7% ee; 5.5 h aliquot: 95.7% Con., 70.6% Sel., 48.6% ee. Almost no aldol is formed as a side product.

Example 4

$Et_2Zn$ (DEZ, 0.9 eq), 2,4-diphenyl-but-3-yn-2-ol (R-(1)) as chiral mediator (0.5 eq), phenylacetylene (a compound of formula III) (2.0 eq), acetophenone (a compound of formula II) (1.0 eq) and HexLi (1 eq) are reacted as described in example 1 wherein the base is added within 10 h and subsequently heating the mixture to r.t. The reaction yields 2,4-diphenyl-but-3-yn-2-ol (R-(1)): 8 h aliquot: 65% Con., 56.2% Sel. 62.3% ee.

Example 5

General procedure for the autocatalytic formation of (S)-5-chloro-α-(cyclopropylethynyl)-2-amino-α-(trifluoromethyl)benzenemethanol (SD573 or (S)-2):

A flask was charged with (1R,2S)—N-pyrrolidinyl-norephedrine ((1S,2R)-PNE, 17.2% in THF/toluene at approx. 90:10 (w/w), 0.3 eq, 0.6 mmol, 0.7 mL), enantiomerically pure (S)-2 (0.18 eq, 0.36 mmol, 104.3 mg). A solution of $Et_2Zn$ (DEZ, 0.24 eq, 1.1 M in toluene, 0.48 mmol, 0.44 mL)

was dropwise added at 17° C., followed by 30 min of stirring at r.t. Cyclopropylacetylene (70.4% in toluene, 2 eq, 4 mmol, 0.42 mL) was added dropwise at 15° C. and the mixture was stirred for additional 1.5 h at r.t. 2-Trifluoromethylcarbonyl-4-chloroaniline (SD570 (a ketoaniline of formula II), 40.4% in THF/toluene, 1 eq, 2 mmol) was added simultaneously with n-hexyllithium (HexLi, 0.9 eq, 2.3 M in hexane, 1.8 mmol, 0.78 mL) to the reaction mixture at 0° C. to 5° C. within 7 h, by means of two syringe pumps. At the completion of addition, reaction mixture was stirred for 2 h at r.t., and then heated to 40° C. After 2 h of stirring at 40° C. the reaction was quenched with citric acid (pH=4 to 6), the aqueous phase was extracted with EtOAc (×3), washed with brine, dried over $MgSO_4$, concentrated and chromatographed on silica gel (Hexane/EtOAc=12:1, (w/w)) to afford tertiary alcohol (S)-2 as a yellowish powder in 87% yield and 90% ee determined by HPLC analysis (Hex/iso-PrOH=85:15, Chiralpack, AD-H, 0.46 cm, Ø×25 cm, flow=1 mL/min, λ=254 nm).

$^1$H NMR (300 MHz, Tol-$d^8$): δ 7.97 (d, J=2.4 Hz, 1H), 7.04 (dd, J=8.4, 2.1 Hz, 1H), 6.07 (d, J=8.7 Hz, 1H), 3.99 (brs, 2H), 3.6 (brs, 1H), 1.054-0.999 (m, 1H), 0.70-0.66 (m, 2H), 0.53-0.48 (m, 2H) ppm; $^{13}$C NMR (75 MHz, $CDCl_3$): δ 143.8, 130.5, 130.3, 126.1, 123.7, 122.3 (q), 120.68, 93.9, 74.8 (q), 70.5, 8.75, 8.7, −0.43 ppm; $^{19}$F NMR (282 MHz, Tol-$d^8$): δ −78.92 ppm.

Example 6

General procedure for the autocatalytic synthesis of (S)—N-(4-chloro-2-(4-cyclopropyl-1,1,1-trifluoro-2-hydroxybut-3-yn-2-yl)phenyl)pivalamide((S)-6) or SD573) with an initial amount of the compound of formula I (SD573) added to the reaction mixture: A flask was charged with (1R,2S)—N-pyrrolidinylnorephedrine (1S,2R)-PNE, 17.2% in THF/toluene at approx. 90:10 (w/w), 0.18 eq, 0.18 mmol, 0.42 mL), enantiomerically pure (S)-6 (0.3 eq, 0.3 mmol, 112.14 mg) and 0.3 mL of THF. A solution of $Et_2Zn$ (DEZ, 0.24 eq, 1.5 M in toluene, 0.24 mmol, 0.32 mL) was dropwise added at 17° C., followed by 30 min of stirring at r.t. Cyclopropylacetylene (70.1% in toluene, 2 eq, 2 mmol, 0.23 mL) was dropwise added at 15° C. and the mixture was stirred for additional 1.5 h at r.t. SD570 (1 eq, 1 mmol, 307.2 mg) in 1 mL THF was added at 5° C. within 30 min, followed by n-hexyllithium (2.2 eq, 2.3 M in hexane, 2.2 mmol, 0.95 mL) to the reaction mixture at 0° C. to 5° C. within 9 h, by means of a syringe pump. At the completion of addition, reaction mixture was stirred for 2 h at r.t., and then heated to 40° C. After 2 h of stirring at 40° C. the reaction was quenched with citric acid (pH=4 to 6), the aqueous phase was extracted with EtOAc (×3), washed with brine, dried over $MgSO_4$, concentrated and chromatographed on silica gel (Hexane/EtOAc=15:1) to afford tertiary alcohol (S)-6 as a yellowish powder in 49% yield and 94% ee (defined by Chiralpak AD-H, 0.46 cm, Ø×25 cm; hexane/iso-PrOH=95:5, flow=1 ml/min, λ=254 nm).

$^1$H NMR (300 MHz, Tol-$d^8$): δ 10.07 (s, 1H), 8.84 (d, J=9 Hz, 1H), 8.17 (d, J=2.4 Hz, 1H), 7.19 (m, 1H), 5.45 (s, 1H), 1.38 (s, 9H), 1.04-0.98 (m, 1H), 0.7-0.66 m, 0.53-0.51 (m, 2H) ppm; $^{13}$C NMR (75 MHz, Tol-$d^8$): δ 177, 138.0, 137.7, 130.8, 128.6, 134.34 (q), 124.72, 124.55, 94.9, 76.95 (q), 70.7, 40.39, 27.63, 8.73, 8.66, −0.3 ppm; $^{19}$F NMR (282 MHz, Tol-$d^8$): δ −78.8 ppm; $[α]_D^{22}$: +5.3 (c 0.09, $CDCl_3$).

The invention claimed is:
1. A process for the preparation of a compound of formula

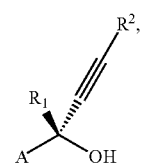

I or mirror image
wherein $R^1$ is selected from the group consisting of hydrogen, $C_{1-6}$-alkyl and ($C_{1-6}$-alkoxy) carbonyl, any alkyl or alkoxy optionally being substituted with one or more halogen atoms,
$R^2$ is selected from the group consisting of aryl, aralkyl, $C_{1-6}$-alkyl and (1'—$R^3$)—$C_{3-6}$-cycloalkyl wherein $R^3$ is hydrogen, methyl or ethyl, any of said aryl, aralkyl, alkyl is optionally substituted with one or more halogen atoms, and
A is selected from the group consisting of $C_{1-20}$-alkyl, $C_{3-6}$-cycloalkyl, aryl and aralkyl, any of said cycloalkyl, aryl and aralkyl is optionally annellated to one or more further 5 to 7 membered carbocyclic or heterocyclic rings, and/or any of said alkyl, cycloalkyl, aryl and aralkyl is optionally substituted with one or more halogen atoms, cyano, $C_{1-6}$-alkyl, $C_{3-6}$-cycloalkyl, —$NR^4R^5$, —$SR^6$ and/or —$OR^7$, and wherein said alkyl and cycloalkyl substituent attached to A is optionally substituted with one or more halogen atoms, and wherein $R^4$ and $R^5$ independently are hydrogen or $C_{1-6}$-alkyl, or wherein $R^4$ is hydrogen and $R^5$ is $C_{2-7}$-acyl or ($C_{1-6}$-alkoxy)carbonyl, wherein each acyl and alkoxy in $R^5$ is optionally substituted with one or more halogen atoms, or wherein $R^4$ and $R^5$ together with the nitrogen atom form a 5 to 7 membered heterocyclic ring, or wherein $R^4$ and $R^5$ together are =CH-aryl, the aryl moiety optionally being substituted with one or more halogen atoms, —$NH_2$, —$NH(C_{1-6}$-alkyl), —$N(C_{1-6}$-alkyl)$_2$ or $C_{1-6}$-alkyl, or $R^4$ and $R^5$ together are =CH—N($C_{1-6}$-alkyl)$_2$, and wherein $R^6$ is $C_{1-6}$-alkyl, optionally substituted with one or more halogen atoms, and wherein $R^7$ is hydrogen or $C_{1-6}$-alkyl, optionally substituted with one or more halogen atoms, or
wherein A and $R^1$ together form a 5 to 7 membered carbocyclic or heterocyclic rings, optionally substituted with one or more halogen atoms, cyano, $C_{1-6}$-alkyl, $C_{3-6}$-cycloalkyl, —$NR^4R^5$, —$SR^6$ and/or —$OR^7$, wherein $R^3$, $R^4$, $R^5$, $R^6$ and $R^7$ are as defined above,
said process comprising the steps of
(i) preparing a mixture of a zinc(II) catalyst, an initial amount of the compound of formula I in a molar ratio to the zinc(II) catalyst from 0.1:1 to 2:1, and optionally a further chiral auxiliary in a molar ratio to the zinc(II) catalyst of 0.1:1 to 3:1, and
(ii) adding to said mixture
(a) a compound of formula

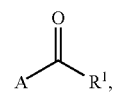

II wherein A and R¹ are as defined above, and
(b) a base, and
(c) a compound of formula

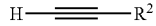  III wherein R² is as defined above,
at a temperature from −78 to 30° C., and
(iii) heating the mixture obtained in step (ii) to 10 to 50° C. until completion of the reaction,
to obtain the compound of formula I.

2. The process of claim 1, wherein the process is carried out in the presence of a proton source selected from the group consisting of $C_{1-6}$-alcohols, benzyl alcohols, phenols and linear or branched $C_{2-5}$-alkanoic acids, each of said $C_{1-6}$-alcohols, phenols and benzyl alcohols optionally being substituted with one or more substituents selected from the group consisting of halogen atoms, nitro, methyl and aryl groups, and said $C_{2-5}$-alkanoic acid optionally being substituted with one or more halogen atoms.

3. The process of claim 1, wherein the zinc(II) catalyst is used in a molar ratio to the compound of formula III from 0.1:1 to 0.3:1.

4. The process of claim 1, wherein the zinc(II) catalyst is selected from the group consisting of di($C_{1-4}$-alkyl)zinc, diphenylzinc, $Zn(OTf)_2$ and $ZnCl_2$, wherein the alkyl moieties are independently selected from the group consisting of methyl, ethyl, propyl, isopropyl, butyl, isobutyl, sec-butyl and tert-butyl.

5. The process of claim 1, wherein in step (i) the product of formula I is added in a molar ratio to the compound of formula III from 0.1:1 to 0.45:1.

6. The process of claim 1, wherein in step (ii) the compound of formula II is used in a molar ratio to the compound of formula III from 0.8:1 to 3:1.

7. The process of claim 1, wherein the base is added in a molar ratio to the compound of formula III from 0.5:1 to 3:1.

8. The process of claim 1, wherein the base is an organometallic compound or a lithium organic salt.

9. The process of claim 8, wherein the organometallic compound is selected from the group consisting of phenyllithium and ($C_{1-8}$-alkyl) lithium.

10. The process of claim 8, wherein the lithium organic salt is a lithium $C_{1-6}$-alkoxide.

11. The process of claim 1, wherein the temperature during the addition of the base is of from −40 to +10° C.

12. The process of claim 1, wherein the reaction is carried out in a non-polar or an aprotic polar or a mixture of aprotic polar and/or non-polar solvents.

* * * * *